(12) United States Patent
Harumatsu et al.

(10) Patent No.: US 9,367,738 B2
(45) Date of Patent: Jun. 14, 2016

(54) METHOD, APPARATUS AND COMPUTER PROGRAM FOR CALCULATING CURRENT DISTRIBUTION INSIDE BRAIN

(71) Applicant: HONDA MOTOR CO., LTD., Tokyo (JP)

(72) Inventors: Masatoshi Harumatsu, Wako (JP); Katsuya Yashiro, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 283 days.

(21) Appl. No.: 14/089,978

(22) Filed: Nov. 26, 2013

(65) Prior Publication Data

US 2014/0163893 A1 Jun. 12, 2014

(30) Foreign Application Priority Data

Dec. 7, 2012 (JP) ................................. 2012-268431

(51) Int. Cl.
| | |
|---|---|
| *G01N 33/48* | (2006.01) |
| *G01N 33/50* | (2006.01) |
| *G06K 9/00* | (2006.01) |
| *G06F 17/11* | (2006.01) |
| *G06F 19/24* | (2011.01) |
| *G06F 19/28* | (2011.01) |
| *G06F 17/10* | (2006.01) |
| *G06F 19/12* | (2011.01) |

(52) U.S. Cl.
CPC .............. *G06K 9/0057* (2013.01); *G06F 17/10* (2013.01); *G06F 17/11* (2013.01); *G06F 19/12* (2013.01); *G06F 19/24* (2013.01); *G06F 19/28* (2013.01)

(58) Field of Classification Search
None
See application file for complete search history.

(56) References Cited

FOREIGN PATENT DOCUMENTS

| | | |
|---|---|---|
| JP | H09253065 A | 9/1997 |
| JP | 2003-038455 A | 2/2003 |

OTHER PUBLICATIONS

Beroza et al. Calculation of amino acid pKas in a protein from a continuum electrostatic model: method and sensitivity analysis. Journal of Computational Chemistry, vol. 17, 1996, pp. 1229-1244.*
Dezhong Yao, "Electric Potential Produced by a Dipole in a Homogeneous Conducting Sphere," IEEE Transactions on Biomedical Engineering, vol. 47, No. 7, Jul. 2000, pp. 964-966.
Jukka Sarvas, "Basic Mathematical and Electromagnetic Concepts of the Biomagnetic Inverse Problem," Phys. Med. Biol., 1987, vol. 32, No. 1, pp. 11-22.
Anne Crouzeix, "Methodes de localisation des generateurs de l'activite electrique cerebrale a partir de signaux electro-et magneto-encepahlographiques," Rapport de these, Institution National des Sciences Appliquees de Lyon, pp. 11-31, 2001.
Japanese Office Action Notification of Reasons for Refusal application No. 2012-268431 mailed Apr. 21, 2015.

* cited by examiner

*Primary Examiner* — Russell S Negin
(74) *Attorney, Agent, or Firm* — Squire Patton Boggs (US) LLP

(57) ABSTRACT

Apparatus for calculating current distribution inside brain includes: initial grid setting unit configured to set grid points constituting grid with predetermined pitch; current calculating unit configured to calculate current value at each grid point based on the electromagnetic information, by solving forward problem to obtain lead field matrix and by solving inverse problem to obtain current source vector; sub-grid setting unit configured to set grid points constituting sub-grid with smaller pitch, only for subset of the previously set grid, based on the current value at each grid point calculated in the preceding current calculating step; and calculation executing unit configured to repeat setting the sub-grid and calculating the current source vector by the sub-grid setting unit and the current calculating unit one or more times, after calculation of current source vector corresponding to the initial grid is executed by the initial grid setting unit and the current calculating unit.

5 Claims, 5 Drawing Sheets

METHOD, APPARATUS AND COMPUTER PROGRAM FOR CALCULATING CURRENT DISTRIBUTION INSIDE BRAIN

CROSS REFERENCE TO RELATED APPLICATION

This application claims the foreign priority benefit under Title 35, United States Code, §119(a)-(d) of Japanese Patent Application No. 2012-268431 filed on Dec. 7, 2012 in the Japan Patent Office, the disclosure of which is herein incorporated by reference in its entirety.

BACKGROUND OF THE INVENTION

1. Technical Field

The present invention relates to a method, an apparatus, and a computer program product for calculating current distribution inside a brain, and in particular to a method, an apparatus, and a computer program product for calculating current distribution inside a brain, by which a solution can be obtained in a short time with a high resolution in-brain current distribution.

2. Description of the Related Art

In recent years, BMI (Brain Machine Interface) has been researched. BMI is a technology for controlling motion of a robot or operation of other devices not by manual control, but by mere thinking about the motion/operation; to operate the robot and other devices, human brain waves (scalp potentials) or brain's magnetic fields (i.e., magnetic fields around a head) are detected in BMI. In BMI, while human brain activity is presumed based on human brain waves or magnetic fields per se, attempts have been made to presume in detail in which part in the human brain (not only on the surface of the head but also at a three-dimensional region within the brain) currents flow, based on this electromagnetic information, to more precisely presume activity within the human brain. A technology for estimating currents inside a human brain based on brain waves is referred to as an EEG (electroencephalography) inverse problem, while a technology for estimating currents inside a human brain based on magnetic fields produced by currents occurring in the brain is referred to as an MEG (magnetoencephalography) inverse problem.

In the EEG inverse problem and the MEG inverse problem, a lead field matrix for deriving an electric potential or a magnetic field from current source distribution (in-brain currents) can be obtained, and the current source can be estimated from this lead field matrix. See, for example, Japanese Laid-open Patent Application Publication No. 2003-38455.

To solve the EEG inverse problem and the MEG inverse problem, the head of a human body can be approximated to a sphere so that currents inside the brain can be calculated at high speeds. See Sarvas, "Basic mathematical and electromagnetic concepts of the biomagnetic inverse problem," Phys. Med. Biol., vol. 32, pp. 11-22, 1987. See also D. Yao, "Potential Produced by a Dipole in a Homogeneous Conducting Sphere," IEEE Trans. Biomed. Eng. vol. 47, pp. 964-966, 2000. However, this method has a problem with precision because the actual shape of the head is not reflected in the calculation. Further, in the case of the MEG inverse problem, there is a property that if a current source faces in the radial direction in a homogenous sphere model, an external magnetic field of the current source becomes zero. This greatly restricts the possibility that in-brain currents can be analyzed.

For this reason, attempts have been made to calculate a current source using various numerical analytical methods which take into account the actual shape of a human head. See A. Crouzeix, "Méthodes de localisation des générateurs de l'activité électrique cérébrale à partir de signaux électro- et magnéto-encépahlographiques", Rapport de thèse, Institution National des Sciences Appliquées de Lyon, pp. 11-31, 2001. In this method, the human head is represented using a mesh model, and current sources are obtained by BEM (Boundary Element Method) or by FEM (Finite Element Method). All references discussed herein, including patent and non-patent literature, are incorporated by reference into the present application. Using these numerical analytical methods, the shape of the human head can be faithfully reflected without restrictions as caused by the sphere approximation, so that in-brain currents can be calculated with high degree of accuracy.

However, these numerical analytical methods require a high degree of computational complexity and thus take considerable computation time. In a numerical analytical method, the complexity is largely dependent on the number of grid points constituting a grid. If a grid with a large pitch is used, the complexity will be reduced accordingly. However, this will cause a decrease in the calculation precision. As a result, a highly precise (high resolution) solution cannot be obtained if the complexity is reduced so much.

In view of the above, it would be desirable to provide a method, an apparatus, and a computer program product for calculating currents inside a brain, by which a solution can be obtained in a short time with a high resolution in-brain current distribution.

SUMMARY OF THE INVENTION

According to a first aspect of the present invention, there is provided a method for calculating current distribution inside a brain using a computer, based on electromagnetic information obtained from a surface of a head, the method. The method comprises: an initial grid setting step of setting grid points constituting a grid with a predetermined pitch; a current calculating step of calculating a current value at each of the grid points based on the electromagnetic information and an equation [L][s]=[b], where [L] is a lead field matrix, [s] is a current source vector that gives current distribution consisting of an array of currents at each of the grid points, and [b] is an electromagnetic vector including an array of the electromagnetic information, by solving a forward problem to obtain [L] and by solving an inverse problem to obtain [s]; and a sub-grid setting step of setting grid points constituting a sub-grid with a pitch smaller than that of a previously set grid, only for a subset of the previously set grid, based on the current value at each grid point calculated in the preceding current calculating step. After the initial grid setting step and the current calculating step are carried out, the sub-grid setting step and the following current calculating step are repeated one or more times.

According to this method, the initial grid setting step and the current calculating step are carried out to calculate a current value at each grid point of the initial grid. Thereafter, in the sub-grid setting step, grid points constituting the sub-grid are set at a pitch smaller than that of the initial grid previously set in the initial grid setting step, only for a subset of the previously set grid, based on the current value at each grid point calculated in the current calculating step. Further, the current calculating step is repeated for the grid including the sub-grid, to obtain a current at each of the grid points.

Accordingly, since a small pitch is applied only to a partial region (subset) and the remaining region (remaining set) has a coarse pitch, the total number of grid points and thus the complexity can be restricted, so that a solution can be obtained in a shorter time. Further, since grid points are set at a smaller pitch in a region where knowing current distribution is desired, current distribution can be obtained at high resolution in the necessary region.

The above method may further comprise a peak grid point detecting step of detecting at least one peak grid point having a peak current value that is a current value higher than current values of grid points surrounding the peak grid point, and the sub-grid setting step may comprise setting the grid points constituting the sub-grid around the peak grid point.

According to this method, a high resolution current distribution can be obtained at a region including the peak grid point having the peak current value.

In the above method, the current calculating step may preferably comprise: setting $[L_i\ 0]$ by adding a zero matrix to a lead field matrix $[L_i]$ for the previously set entire grid such that $[L_i\ 0]$ has a size of an array corresponding to a lead field matrix $[L_{i+1}]$ for the currently set entire grid; setting $[0\ L_{si}]$ by adding a zero matrix to a lead field matrix $[L_{si}]$ for the currently set sub-grid such that $[0\ L_{si}]$ has a size of an array corresponding to the lead field matrix $[L_{i+1}]$ for the currently set entire grid; solving a forward problem to obtain $[0\ L_{si}]$ based on the electromagnetic vector $[b]$; and calculating $[L_{i+1}]$ by $[L_{i+1}]=[L_i\ 0]+[0\ L_{si}]$.

According to this method, since the forward problem is solved only for the lead field matrix $[0\ L_{si}]$ having the number of elements corresponding to the increased grid points, and the solved $[0\ L_{si}]$ is added to the lead field matrix having been calculated in the previous step to obtain $[L_i\ L_{si}]$. This can greatly reduce the complexity compared to solving a forward problem for the lead field matrix for the entire region.

In the above method, the current calculating step comprises a step of solving an inverse problem using a gram matrix $[G]$ $(=[L][L]^T)$ by calculating $[G_{i+1}]=[G_i]+[L_{si}][L_{si}]^T$, where $[G_i]$ is a gram matrix for the previously set entire grid, $[G_{i+1}]$ is a gram matrix for the currently set entire grid, and $[L_{si}]$ is a lead field matrix for the currently set sub-grid.

According to this method, the complexity can be reduced compared to the method for obtaining a gram matrix $[G_{i+1}]$ for the currently set entire grid by solving $[L_{i+1}][L_{i+1}]^T$.

According to a second aspect of the present invention, there is provided an apparatus for calculating current distribution inside a brain, based on electromagnetic information obtained from a surface of a head. The apparatus comprises: an initial grid setting unit configured to set grid points constituting a grid with a predetermined pitch; a current calculating unit configured to calculate a current value at each of the grid points based on the electromagnetic information and an equation $[L][s]=[b]$, where $[L]$ is a lead field matrix, $[s]$ is a current source vector that gives current distribution consisting of an array of currents at each of the grid points, and $[b]$ is an electromagnetic vector including an array of the electromagnetic information, by solving a forward problem to obtain $[L]$ and by solving an inverse problem to obtain $[s]$; a sub-grid setting unit configured to set grid points constituting a sub-grid with a pitch smaller than that of a previously set grid, only for a subset of the previously set grid, based on the current value at each grid point calculated in the preceding current calculating step; and a calculation executing unit configured to repeat setting of the sub-grid and calculation of the current source vector $[s_{i+1}]$ by the sub-grid setting unit and the current calculating unit one or more times, after calculation of a current source vector $[s_1]$ corresponding to the initial grid is executed by the initial grid setting unit and the current calculating unit.

Further, according to a third aspect of the present invention, there is provided a computer program stored on a computer-readable storage medium, for calculating current distribution inside a brain using a computer, based on electromagnetic information obtained from a surface of a head. The computer program configures the computer upon being read and executed by the computer to perform the functions of: an initial grid setting unit configured to set grid points constituting a grid with a predetermined pitch; a current calculating unit configured to calculate a current value at each of the grid points based on the electromagnetic information and an equation $[L][s]=[b]$, where $[L]$ is a lead field matrix, $[s]$ is a current source vector that gives current distribution consisting of an array of currents at each of the grid points, and $[b]$ is an electromagnetic vector including an array of the electromagnetic information, by solving a forward problem to obtain $[L]$ and by solving an inverse problem to obtain $[s]$; a sub-grid setting unit configured to set grid points constituting a sub-grid with a pitch smaller than that of a previously set grid, only for a subset of the previously set grid, based on the current value at each grid point calculated in the preceding current calculating step; and a calculation executing unit configured to repeat setting of the sub-grid and calculation of the current source vector $[s_{i+1}]$ by the sub-grid setting unit and the current calculating unit one or more times, after calculation of a current source vector $[s_1]$ corresponding to the initial grid is executed by the initial grid setting unit and the current calculating unit.

BRIEF DESCRIPTION OF THE DRAWINGS

Other objects and aspects of the present invention will become more apparent by describing in detail illustrative, non-limiting embodiments thereof with reference to the accompanying drawings, in which:

FIGS. 2A and 2B are views explaining setting of a sub-grid, in which FIG. 2A shows a grid before setting a sub-grid, and FIG. 2B shows a grid after setting a sub-grid;

DETAILED DESCRIPTION OF THE INVENTION

With reference to the drawings, one embodiment of the present invention will be described in detail. A calculation apparatus 100 for calculating currents inside a brain according to one embodiment calculates current distribution inside the brain, based on an electromagnetic vector $[b]$ (vector representing a set containing information about brain waves or brain's magnetic fields) such as brain waves obtained by measuring electric potentials on the surface of the scalp or brain's magnetic fields obtained by measuring magnetic fields in the vicinity of the scalp, and in particular calculates a current source vector $[s]$ by which the electromagnetic vector $[b]$ has been generated. The number of elements of the electromagnetic vector $[b]$ is the same as the number of sensors, and usually dozens of elements up to several tens of elements are present. Meanwhile, the number of elements of the current source vector [s] is the same as the number of grid points constituting the grid of the in-brain model, and usually several thousand elements up to several tens of thousands of elements are present.

Figure 1:
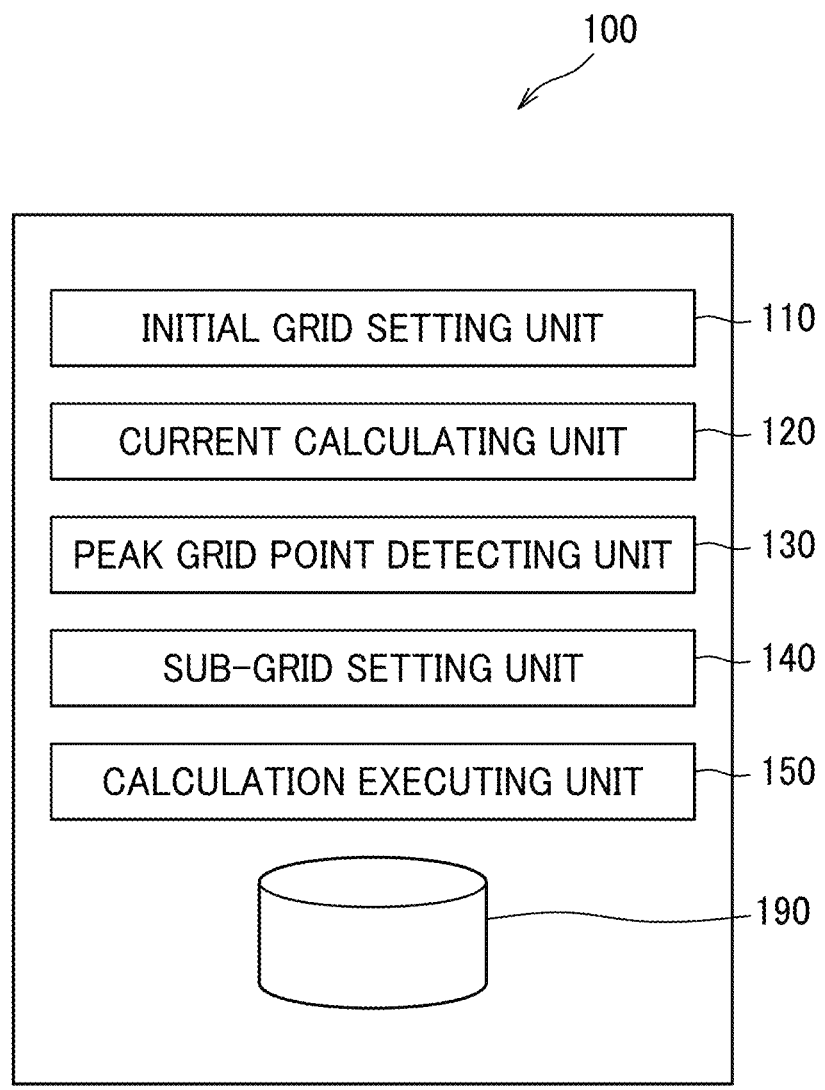
FIG. 1 is a block diagram illustrating a calculation apparatus for calculating currents inside a human brain according to one exemplary embodiment of the present invention.

To perform the above calculation, as shown in FIG. 1, the calculation apparatus 100 includes, as means for calculating currents inside a brain, an initial grid setting unit 110, a current calculating unit 120, a peak grid point detecting unit 130, a sub-grid setting unit 140, and a calculation executing unit 150. The calculation apparatus 100 is implemented in a computer including a CPU, a ROM, a RAM, and a storage device such as an external memory (these components are not shown in the figures), and when a computer program is loaded where necessary into the RAM and the CPU executes the program, the computer performs the functions of these unit. Further, the calculation apparatus 100 includes a storage unit 190 for storing variables, etc. such as coordinate data of a grid, a lead field matrix [L], an electromagnetic vector [b], a current source vector [s], and a gram matrix [G].

The initial grid setting unit 110 is configured to set grid points constituting a grid with a predetermined pitch (i.e., initial grid). Setting of the initial grid is performed by defining space coordinates in a manner similar to the conventional method. Preferably, in accordance with the computing capability of the computer used in practice, the initial grid is set at a relatively large (coarse) pitch such that calculation of currents can be performed in a relatively short period of time. For example, the initial grid can be set at about 10 mm pitch in view of the actual size of the human brain. In this instance, the number of grid points can be limited approximately to 1200.

The current calculating unit 120 is configured to calculate a current source vector [s] from an electromagnetic vector [b] using the grid having been set by the initial grid setting unit 110 and/or the sub-grid setting unit 140. Herein, the term "grid" indicates both the initial grid and the sub-grid. The basic idea of calculating currents is to calculate a current value at each of the grid points based on the electromagnetic information and an equation [L][s]=[b], where [L] is a lead field matrix, [s] is a current source vector that gives current distribution consisting of an array of currents at each of the grid points, and [b] is an electromagnetic vector including an array of the electromagnetic information, by solving a forward problem to obtain [L] and by solving an inverse problem to obtain [s].

To be more specific, the relation among the current source vector [s], the lead field matrix [L] and the electromagnetic vector [b] can be represented by [L][s]=[b]. To solve the forward problem, [b] is obtained by assigning 1 to the k-th current element of the current source vector [s] while assigning 0 to the other current elements. The obtained [b] vector corresponds to the k-th column vector element in the lead field matrix [L]. This processes is sequentially repeated to determine the elements of [L].

Once the lead field matrix [L] is determined, the current source vector [s] can be solved by various methods for solving the inverse problem for the above formula.

To solve the inverse problem, for example, the following methods can be used. Since the current source vector [s] has a larger number of elements than the electromagnetic vector [b] as described above and has a smaller number of equations for unknowns, the solution cannot be determined uniquely for each unknown. In the current source vector [s] obtained by the following methods, all the elements are estimated solutions.

The equation for solving the current source vector [s] may be expressed, using a weighting matrix [w], by the general formula: $[s]=[w]^T[b]$, and [w] can be solved by each of the following methods (1) to (10). In each of the following formulae, [G] represents a gram matrix $(=[L][L]^T)$, and [R] represents a covariance matrix of [b].

(1) Minimum norm method $$[W]=[G]^{-1}[L]$$

(2) Weighted minimum norm method $$[W]=[G]^{-1}[L]([L]^T[G]^{-2}[L])^{-1/2}$$

(3) WROP (Weighted resolution optimization) method $$[W]=[G]^{-1}[L]([L]^T[G]^{-1}[L])^{-1}$$

(4) Array-gain constraint WROP method $$[W]=[G]^{-1}[\tilde{L}]([\tilde{L}]^T[G]^{-1}[\tilde{L}])^{-1}$$

$$[\tilde{L}]=[L]/\|[L]\|$$

(5) sLORETA (standardized low resolution brain electromagnetic tomography) method $$[W]=[G]^{-1}[L]([L]^T[G]^{-1}[L])^{-1/2}$$

(6) Time-averaged minimum norm method $$[W]=[R]^{-1}[L]$$

(7) Weighted minimum variance method $$[W]=[R]^{-1}[L]([L]^T[R]^{-2}[L])^{-1/2}$$

(8) Minimum variance method $$[W]=[R]^{-1}[L]([L]^T[R]^{-1}[L])^{-1}$$

(9) Array-gain constraint minimum variance method $$[W]=[R]^{-1}[\tilde{L}]([\tilde{L}]^T[R]^{-1}[\tilde{L}])^{-1}$$

(10) Time-averaged sLORETA method $$[W]=[R]^{-1}[L]([L]^T[R]^{-1}[L])^{-1/2}$$

In the calculation at the second time or later, the sub-grid is set by the sub-grid setting unit 140, and the current calculating unit 120 calculates the lead field matrix $[L_{i+1}]$ for the currently set entire grid (i.e., after the latest sub-grid has been set) as follows:

First, the lead field matrix $[L_i]$ for the previously set entire grid is set to have a size of an array corresponding to the lead field matrix $[L_{i+1}]$. Herein, $[L_{i+1}]$ has the same number of rows as $[L_i]$, however, the number of columns of $[L_{i+1}]$ has been increased according to increase in the number of unknowns of the added sub-grid. For this reason, $[L_i\ 0]$ is set by adding a zero matrix to $[L_i]$. Similarly, the lead field matrix $[L_{si}]$ for the currently set sub-grid is set to have a size of an array corresponding to the lead field matrix $[L_{i+1}]$. For this reason, $[0\ L_{si}]$ is set by adding a zero matrix to $[L_{si}]$. Thereafter, $[0\ L_{si}]$ is obtained by solving the forward problem based on the input electromagnetic vector [b], and $[L_{i+1}]$ is obtained by calculating $[L_{i+1}]=[L_i\ 0]+[0\ L_{si}]$.

Accordingly, the forward problem is solved only for the lead field matrix $[0\ L_{si}]$ having the number of elements corresponding to the grid points increased by the sub-grid setting unit 140, and the solved $[0\ L_{si}]$ is added to the lead field matrix having been calculated in the previous step to obtain $[L_i\ L_{si}]$ $(=[L_{i+1}])$. Since the complexity for solving the forward problem accounts for a large portion of the calculation required for solving the current source vector [s], this method can greatly reduce the complexity compared to any other methods of solving the forward problem of the lead field matrix $[L_i\ L_{si}]$ for the entire region.

Further, to solve the above inverse problem using the gram matrix [G], it is preferable that the current calculating unit 120 calculates $[G_{i+1}]=[G_i]+[L_{si}][L_{si}]^T$, where $[G_i]$ is a gram matrix for the previously set entire grid, $[G_{i+1}]$ is a gram matrix for the currently set entire grid, and $[L_{si}]$ is a lead field matrix for the currently set sub-grid.

With this configuration, it is possible to obtain the same solution as obtained by calculating $[L_{i+1}][L_{i+1}]^T$ as described below.

$$
\begin{aligned}
[G_{i+1}] &= [L_{i+1}][L_{i+1}]^T \\
&= [[L_i \ 0] + [0 \ L_{si}]][[L_i \ 0] + [0 \ L_{si}]]^T \\
&= [L_i \ 0][L_i \ 0]^T + [L_i \ 0][0 \ L_{si}]^T + \\
&\quad [0 \ L_{si}][L_i \ 0]^T + [0 \ L_{si}][0 \ L_{si}]^T \\
&= [L_i][L_i]^T + [0] + [0] + [L_{si}][L_{si}]^T \\
&= [G_i] + [L_{si}][L_{si}]^T
\end{aligned}
$$

With this configuration of the current calculating unit 120, since the calculation of $[G_i]$ has been completed, $[L_{si}][L_{si}]^T$ is calculated and the obtained $[L_{si}][L_{si}]^T$ is added to $[G_i]$. Therefore, $[G_{i+1}]$ can be obtained by a reduced complexity.

The peak grid point detecting unit 130 is configured to detect at least one peak grid point having a peak current value that is a current value higher than current values of grid points surrounding the peak grid point, based on the current value at each of the grid points calculated by the current calculating unit 120. The peak grid points can be detected by various known method. As an example, a plurality of grid points are detected each of which has a current value higher than those of the proximating grid points on the top, bottom, right, left, front, and back of the subject grid point. Thereafter, of these detected grid points, a predetermined number of grid points having a higher current value are selected, so that grid points having a peak current value can be detected. The number of peak grid points to be detected can be changed in accordance with the subject data for calculation, such as brain waves and brain's magnetic fields. Selecting an unnecessarily large number of peak grid points may result in picking up of fine noise and thus setting of the sub-grid in an unnecessarily wide range. As a result, the complexity is increased. The number of peak grid points can be increased or decreased where necessary in accordance with the method used for solving the inverse problem or the number of peak currents inside the brain. In general, the number of peak grid points in the range from 5 to 50 is preferable, and the smaller the better. In the case of insufficient detection of the peak grid points, it is preferable to increase the number of peak grid points.

The sub-grid setting unit 140 is configured to set grid points constituting the sub-grid at a pitch smaller than that of the previously set grid, only for a subset of the previously set grid, based on the current value at each grid point calculated by the current calculating unit 120. In this embodiment, in order to subject the current distribution around peak grid points to calculation at high resolution, the sub-grid is set in a region including the peak grid point(s) detected by the peak grid point detecting unit 130.

Figure 2A:
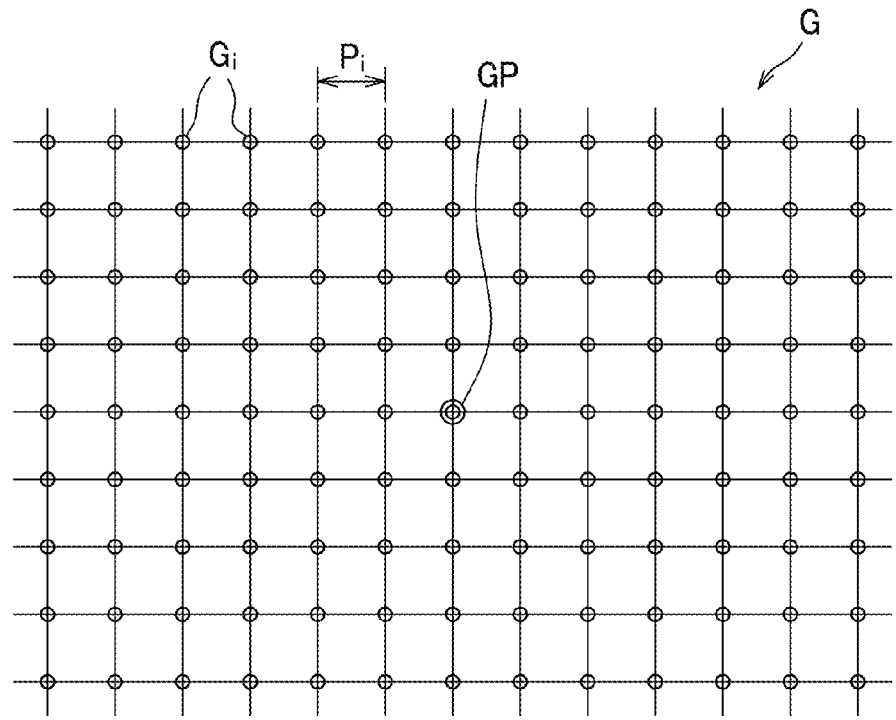
Figure 2B:
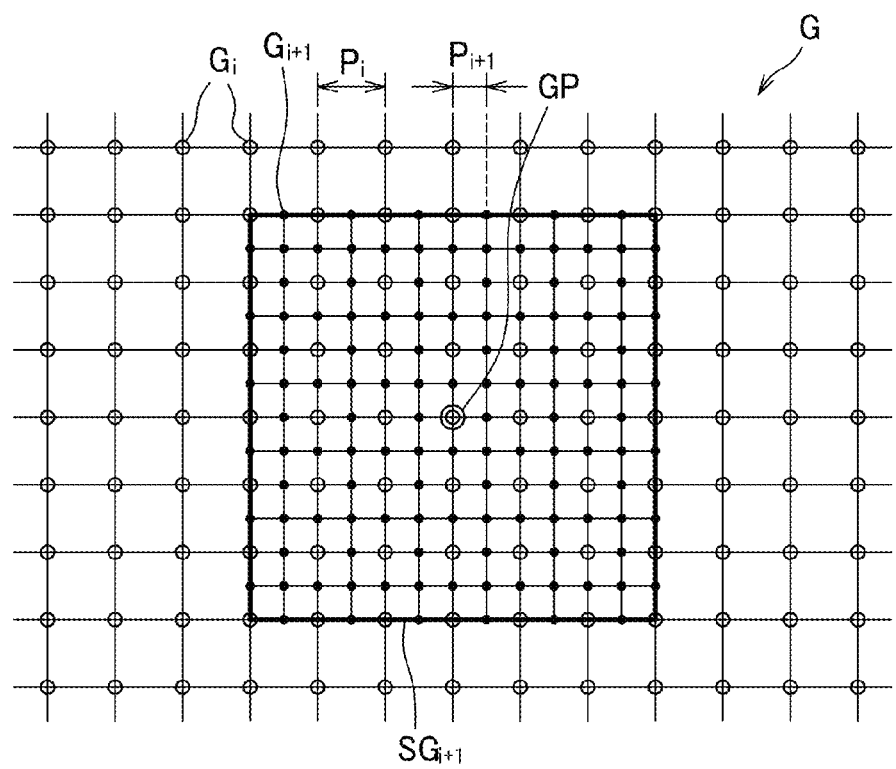

For example, in the case where the grid G consisting of the grid points $G_i$, has been set in a region including a peak grid point GP at a pitch $P_i$, (see FIG. 2A), the sub-grid setting unit 140 sets new grid points $G_{i+1}$ in a region including the peak grid point GP at a pitch $P_{i+1}$ smaller than the pitch $P_i$ (see FIG. 2B). The grid with this smaller pitch $P_{i+1}$ is set within a cubic region defined by six sides containing six grid points $G_{i+1}$ located at the top, bottom, right, left, front and back of a peak grid point GP with a distance of Nr×$P_i$ (Nr is the number of gird points $G_{i+1}$ predetermined to define the size of the cubic region; FIG. 2 shows the grid in two dimension for the purpose of convenience). According to the invention, a newly defined grid consisting of the new grid points $G_{i+1}$ for interpolating the grid points $G_i$ and having the pitch $P_{i+1}$ is referred to as a sub-grid $SG_{i+1}$. In the example shown in FIG. 2B, Nr is 3 and the pitch $P_{i+1}$ is $P_i/2$. However, they may be determined as appropriate. For example, Nr may be any number selected from 2, 3, 4 and 5, and the pitch $P_{i+1}$ may be selected from a range of $P_i/2$ to $p_i/5$. Further, the shape of the region of the sub-grid $SG_{i+1}$ is not limited to a cubic shape, and a spherical region, for example, may be applicable. Further, if the peak grid points GP are arranged in line, the sub-grid setting region may be set as a rectangular parallelepiped or a circular cylinder extending along the line. In this instance, setting Nr to a smaller value in a direction orthogonal to the line makes it possible to reduce the size of the sub-grid $SG_{i+1}$ and to increase the resolution of the current distribution in the region including the peak grid points GP.

The calculation executing unit 150 is configured to repeat one or more times the setting of the sub-grid by the sub-grid setting unit 140 and the calculation of the current source vector $[S_{i+1}]$ by the current calculating unit 120 based on the new grid consisting of the sub-grids, after the initial grid setting unit 110 executing the setting of the initial grid and the current calculating unit 120 executing the calculation of the current source vector $[S_1]$ based on the initial grid. In other words, the calculation executing unit 150 is means for executing a process corresponding to a main flow of the computer program.

The number of repeating the sub-grid setting step and the current calculating step by the calculation executing unit 150 (hereinafter referred to as an "iteration count") may be set as appropriate in accordance with the subject data for calculation.

With reference to the flowchart of FIG. 3 and a model shown in FIGS. 4 to 6, description will be given of the calculation process (calculation method) for calculating currents inside the brain executed by the calculation apparatus 100 configured as described above.

Figure 3:
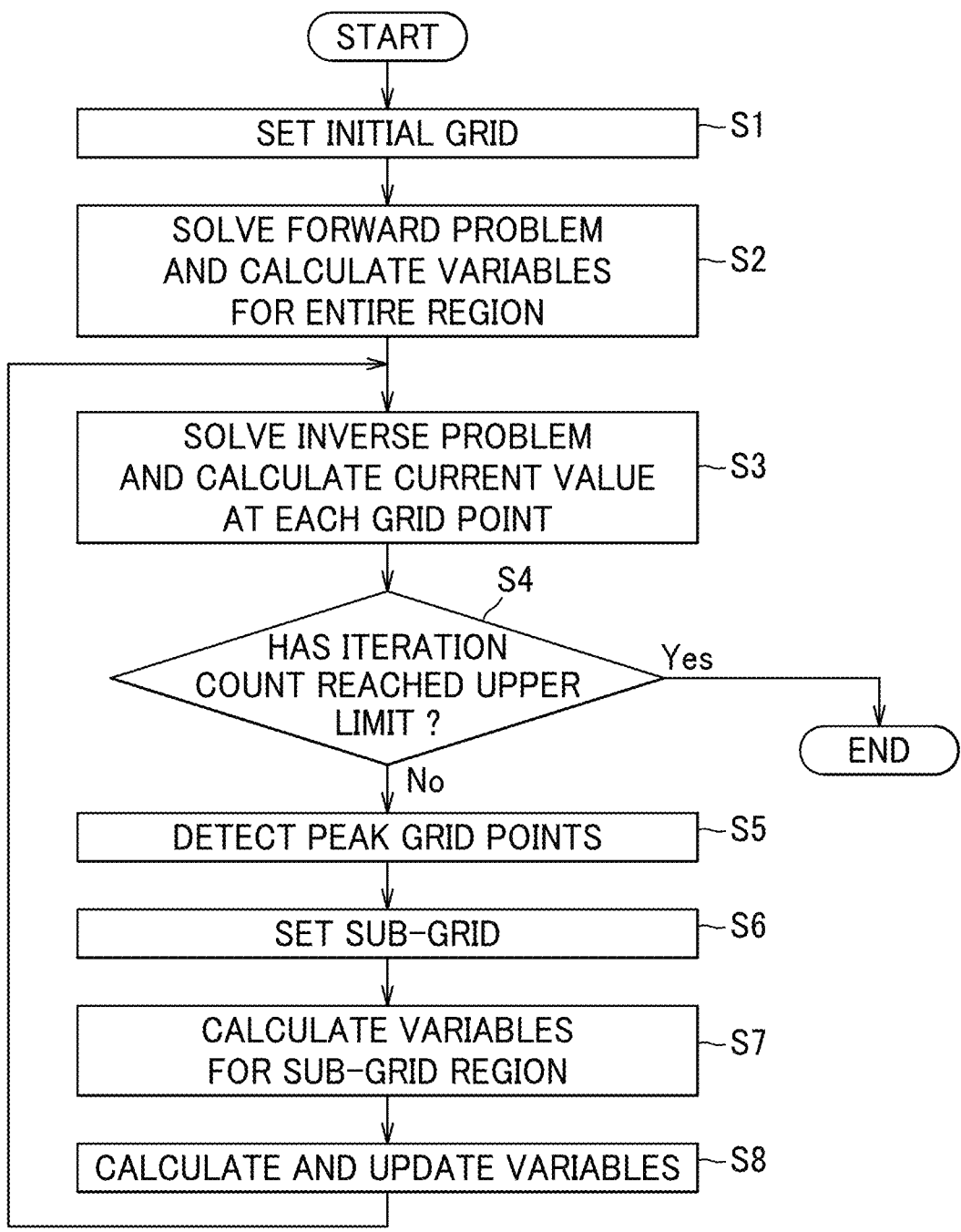
FIG. 3 is a flowchart for explaining a calculation process for calculating currents inside the brain.

The entire process shown in FIG. 3 is controlled by the calculation executing unit 150 and carried out as follows.

Figure 4:
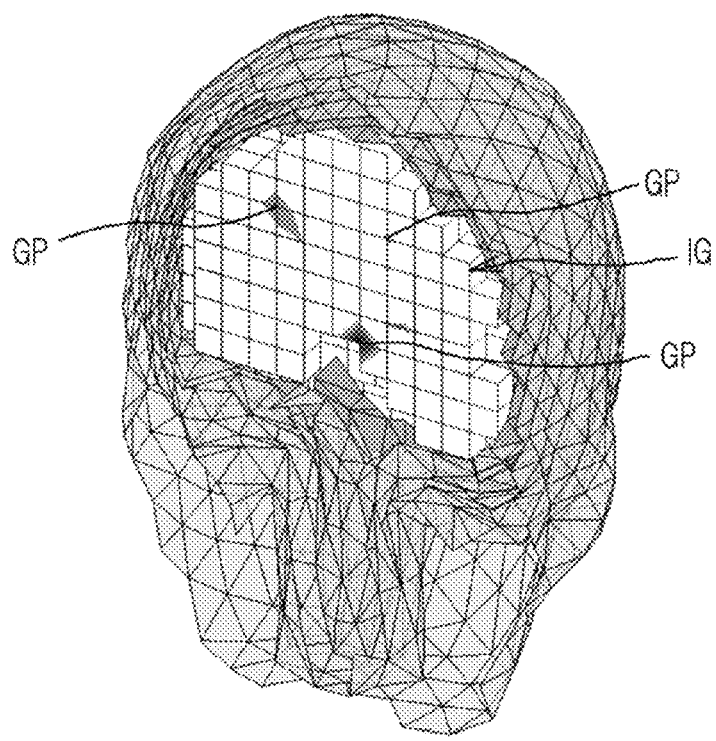
FIG. 4 shows an example of a surface mesh model of a human head and an initial grid inside the brain.

First, as seen in FIG. 4, the initial grid setting unit 110 sets an initial grid IG with a pitch $P_1$ in a region corresponding to a region inside a human brain (S1: initial grid setting step).

Next, for the initial grid IG, the current calculating unit 120 calculates a lead field matrix $[L_1]$ by solving a forward problem based on an input electromagnetic vector [b] (S2: current calculating step). The current calculating unit 120 then calculates other variables for the entire region, such as a gram matrix [G], a covariance matrix [R], and a weighting matrix [w], as selected depending on the method used for solving the inverse problem. The variables thus calculated are stored in the storage unit 190. In the following description, detailed description for storing the calculation results and the calculation process into the storage unit 190 will be omitted.

Thereafter, the current calculating unit 120 calculates the current value at each grid point $G_1$ (i.e., current source vector $[s_1]$) by solving the inverse problem using the weighting matrix [w] (S3: current calculating step). After calculation of the current values, the calculation executing unit 150 determines whether or not the iteration count has reached the upper limit. If the calculation executing unit 150 determines that the iteration count has been reached the upper limit (S4: Yes), then the calculation executing unit 150 completes the process. If the calculation executing unit 150 determines that the iteration count has not reached the upper limit (S4: No), the operation of the calculation executing unit 150 goes to step S5 for setting a sub-grid and re-calculating current values.

The peak grid point detecting unit 130 detects peak values until the iteration count reaches the upper limit (S5; peak grid point detecting step). Accordingly, in the example shown in FIG. 4, three peak grid points GP have been detected in the displayed section.

Figure 5:
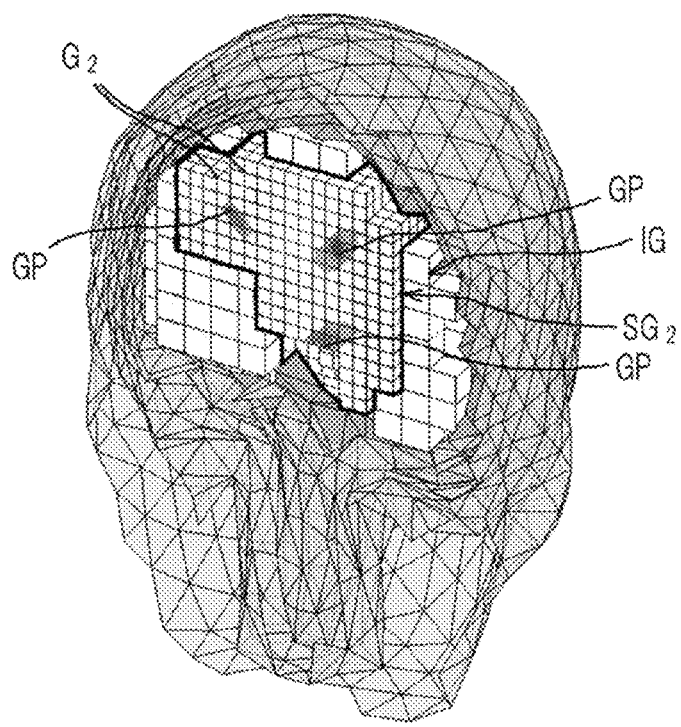
FIG. 5 shows an example of a surface mesh model of the human head and an in-brain grid, when a sub-grid is set in the brain for the first time.

Next, as seen in FIG. 5, the sub-grid setting unit 140 sets new grid points $G_2$ for each of the peak grid points GP detected by the peak grid point detecting unit 130, within a predetermined region including the peak grid point GP, so that a sub-grid $SG_2$ is set for each of the predetermined regions (S6: sub-grid setting step). Thereafter, the current calculating unit 120 calculates variables for the entire region of the sub-grid (S7: current calculating step). Namely, in order to make the lead field matrix $[L_{si}]$ corresponding to the newly set grid points $G_2$ to have the size of the array corresponding to $[L_2]$, a zero matrix is added to set $[0 \ Ls_1]$, and then $[0 \ L_{si}]$ is obtained by solving the forward problem based on the electromagnetic vector [b].

Next, the variables for the entire grid are calculated and updated (S8: current calculating step). The calculation of the variables in this step is carried out as follows. For the lead field matrix $[L_2]$, in order to make the lead field matrix $[L_1]$ to have the size of the array corresponding to $[L_2]$, a zero matrix is added to set $[L_1 \ 0]$, and then the newly set lead field matrix $[L_2]$ is calculated by $[L_2]=[L_1 \ 0]+[0 \ L_{si}]$. If a gram matrix [G] is used to solve the inverse problem, $[G_2]$ is calculated by $[G_2]=[G_1]+[L_{si}][L_{si}]^T$.

Thereafter, the operation of the calculation executing unit 150 returns to step S3, and the calculation of current values, the setting of the sub-grid $SG_i$, and the calculation of the current source vector $[s_i]$ are repeated for the required number of times (S4-S8; S3).

Figure 6:
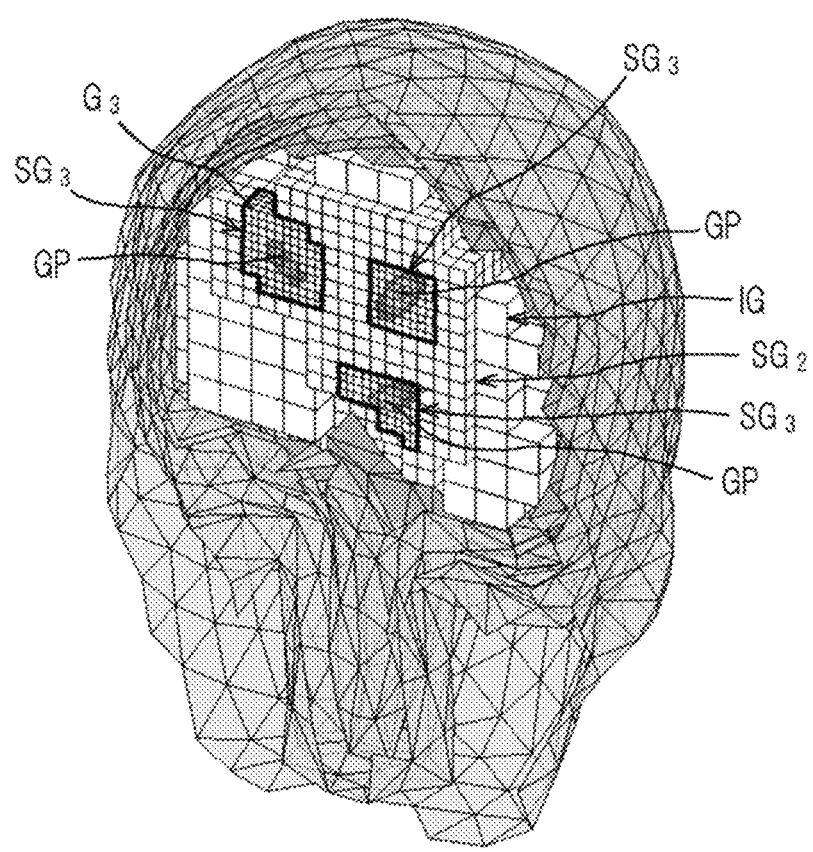
FIG. 6 shows an example of a surface mesh model of the human head and an in-brain grid, when the sub-grid is set in the brain for the second time.

Accordingly, in the case of the example shown in FIGS. 4 to 6, peak grid points GP are re-detected after setting the sub-grid $SG_2$ (see FIG. 5), and a finer sub-grids $SG_3$ is set for each region including the corresponding peak grid point (see FIG. 6). As seen in FIG. 6, calculating current source vectors $[s_3]$ after setting the sub-grids $SG_3$ makes it possible to obtain a high resolution current distribution in each region including the peak grid point GP.

According to the calculation apparatus 100 (computer program) for calculating currents inside the brain and the calculation method by this calculation apparatus 100 as described above in this embodiment, a high resolution current distribution can be obtained in each region including the peak grid point by setting a sub-grid smaller than the initial grid, whereas in a region remote from the peak grid points a grid with a coarse pitch is set. Accordingly, since the total number of grid points does not increase so much, it is possible to calculate currents inside the brain in a short time because the complexity is reduced.

Further, to calculate current values at the second time or later, the lead field matrix $[L_{i+1}]$ is calculated by $[L_{i+1}]=[L_i \ 0]+[0 \ L_{si}]$. This can reduce the complexity, and the current distribution inside the brain can be obtained in a short time. Further, if a gram matrix [G] is used to solve the inverse problem, the gram matrix $[G_{i+1}]$ is calculated by $[G_{i+1}]=[G_i]+[L_{si}][L_{si}]^T$. This can reduce the complexity, and the current distribution inside the brain can be obtained in a short time.

The comparison of the complexity will be briefly described below.

Assuming that time t is required for calculating currents inside the brain for a reference grid (e.g., initial grid) having a reference pitch, 8 t is required if a half (½) pitch is applied to the entire region, and 64 t is required if a quarter (¼) pitch is applied to the entire region.

In contrast, as with the above embodiment, if a sub-grid is applied to a partial region (subset) to calculate currents inside the brain, the calculation time is expressed as follows, on the assumption that the distance from a peak grid point to each of the proximating grid points is two times of the pitch (Nr=2), and the number of peak grid points is 5 (Np=5):

2 t+g, if the iteration count is 1, and the sub-grid with a half pitch of the reference pitch is set, and 4 t+2 g, if the iteration count is 2, and the sub-grid with a quarter pitch of the reference pitch is set.

Herein, g is time required for the following operations (1) to (3).

(1) The size of the lead field matrix increases because of the formation of the sub-grid, and it is necessary to extend the calculating area (i.e., to allocate memory) for storing data increased from the original lead field matrix and to write sub-grid-related data in the calculating area. Accordingly, time g is required for the memory allocation and the writing of the sub-grid-related data.

(2) Adding the sub-grid causes hexahedron elements to be changed when displaying the calculation results of the current distribution inside the brain. Accordingly, time g is required for rewriting information about grid points constituting the new hexahedron elements.

(3) If detected peak grid points are close to each other, proximating grid points constituting sub-grids and surrounding these grid points may overlap one another. Accordingly, time g is required for bringing these overlapped grid points together.

Since time g required for the above operations is extremely short as compared to t, the calculation apparatus 100 according to this embodiment can calculate the current distribution inside the brain in an extremely short period of time.

Although the present invention has been described in detail with reference to the above exemplary embodiment, the present invention is not limited to this specific embodiment and various changes and modifications may be made without departing from the scope of the appended claims.

In the above embodiment, the sub-grid is set in a region surrounding each of the peak grid points. However, the sub-grid setting region is not limited to a region surrounding a peak grid point. For example, the sub-grid setting region may be set as a region surrounding a grid point having a predetermined current value.

What is claimed is:

1. A method for calculating current distribution inside a brain using a computer, based on electromagnetic information obtained from a surface of a head, the method comprising:
   an initial grid setting step of setting grid points constituting a grid with a predetermined pitch;
   a current calculating step of calculating a current value at each of the grid points based on the electromagnetic information and an equation $[L][s]=[b]$, where [L] is a lead field matrix, [s] is a current source vector that gives current distribution consisting of an array of currents at each of the grid points, and [b] is an electromagnetic vector including an array of the electromagnetic information, by solving a forward problem to obtain [L] and by solving an inverse problem to obtain [s]; and
   a sub-grid setting step of setting grid points constituting a sub-grid with a pitch smaller than that of a previously set grid, only for a subset of the previously set grid, based on the current value at each grid point calculated in the preceding current calculating step, wherein after the initial grid setting step and the current calculating step are carried out, the sub-grid setting step and the following current calculating step are repeated one or more times, and wherein the current calculating step comprises a step of solving an inverse problem [G] by calculating $[G_{i+1}]=[G_i]+[L_{si}][L_{si}]^T$, where $[G_i]$ is a gram matrix for the previously set entire grid, $[G_{i+1}]$ is a gram matrix for the currently set entire grid, and $[L_{si}]$ is a lead field matrix for the currently set sub-grid.

2. The method according to claim 1, further comprising a peak grid point detecting step of detecting at least one peak grid point having a peak current value that is a current value higher than current values of grid points surrounding the at least one peak grid point, wherein the sub-grid setting step comprises setting the grid points constituting the sub-grid around the at least one peak grid point.

3. The method according to claim 1, wherein the current calculating step comprising:

setting $[L_i\ 0]$ by adding a zero matrix to a lead field matrix $[L_i]$ for the previously set entire grid such that $[L_i\ 0]$ has a size of an array corresponding to a lead field matrix $[L_{i+1}]$ for the currently set entire grid;

setting $[0\ L_{si}]$ by adding a zero matrix to a lead field matrix $[L_{si}]$ for the currently set sub-grid such that $[0\ L_{si}]$ has a size of an array corresponding to the lead field matrix $[L_{i+1}]$ for the currently set entire grid;

solving a forward problem to obtain $[0\ L_{si}]$ based on the electromagnetic vector [b]; and calculating $[L_{i+1}]$ by $[L_{i+1}]=[L_i\ 0]+[0\ L_{si}]$.

4. An apparatus for calculating current distribution inside a brain, based on electromagnetic information obtained from a surface of a head, the apparatus comprising:

an initial grid setting unit configured to set grid points constituting a grid with a predetermined pitch;

a current calculating unit configured to calculate a current value at each of the grid points based on the electromagnetic information and an equation [L][s]=[b], where [L] is a lead field matrix, [s] is a current source vector that gives current distribution consisting of an array of currents at each of the grid points, and [b] is an electromagnetic vector including an array of the electromagnetic information, by solving a forward problem to obtain [L] and by solving an inverse problem to obtain [s];

a sub-grid setting unit configured to set grid points constituting a sub-grid with a pitch smaller than that of a previously set grid, only for a subset of the previously set grid, based on the current value at each grid point calculated in the preceding current calculating step; and a calculation executing unit configured to repeat setting of the sub-grid and calculation of the current source vector $[s_{i+1}]$ by the sub-grid setting unit and the current calculating unit one or more times, after calculation of a current source vector $[s_1]$ corresponding to the initial grid is executed by the initial grid setting unit and the current calculating unit, wherein the current calculating unit is further configured to solve an inverse problem using a gram matrix [G] by calculating $[G_{i+1}]=[G_i]+[L_{si}][L_{si}]^T$, where $[G_i]$ is a gram matrix for the previously set entire grid, $[G_{i+1}]$ is a gram matrix for the currently set entire grid, and $[L_{si}]$ is a lead field matrix for the currently set sub-grid.

5. A computer program stored on a non-transitory computer-readable storage medium, for calculating current distribution inside a brain using a computer, based on electromagnetic information obtained from a surface of a head, the computer program configuring the computer upon being read and executed by the computer to perform the functions of:

an initial grid setting unit configured to set grid points constituting a grid with a predetermined pitch;

a current calculating unit configured to calculate a current value at each of the grid points based on the electromagnetic information and an equation [L][s]=[b], where [L] is a lead field matrix, [s] is a current source vector that gives current distribution consisting of an array of currents at each of the grid points, and [b] is an electromagnetic vector including an array of the electromagnetic information, by solving a forward problem to obtain [L] and by solving an inverse problem to obtain [s];

a sub-grid setting unit configured to set grid points constituting a sub-grid with a pitch smaller than that of a previously set grid, only for a subset of the previously set grid, based on the current value at each grid point calculated in the preceding current calculating step; and a calculation executing unit configured to repeat setting of the sub-grid and calculation of the current source vector $[s_{i+1}]$ by the sub-grid setting unit and the current calculating unit one or more times, after calculation of a current source vector $[s_1]$ corresponding to the initial grid is executed by the initial grid setting unit and the current calculating unit, wherein the current calculating unit is further configured to solve an inverse problem using a gram matrix [G] by calculating $[G_{i+1}]=[G_i]+[L_{si}][L_{si}]^T$, where $[G_i]$ is a gram matrix for the previously set entire grid, $[G_{i+1}]$ is a gram matrix for the currently set entire grid, and $[L_{si}]$ is a lead field matrix for the currently set sub-grid.

* * * * *